United States Patent [19]

Wahl et al.

[11] Patent Number: 5,545,620
[45] Date of Patent: Aug. 13, 1996

[54] SYNTHETIC FIBRONECTIN FRAGMENTS AS INHIBITORS OF RETROVIRAL INFECTION

[75] Inventors: Sharon M. Wahl, Gaithersburg, Md.; James B. McCarthy; Leo T. Furcht, both of Minneapolis, Minn.

[73] Assignees: The United States of America as represented by the Department of Health and Human Services, Washington, D.C.; Reagents of the University of Minnesota, Minneapolis, Minn.

[21] Appl. No.: 291,349

[22] Filed: Aug. 16, 1994

Related U.S. Application Data

[63] Continuation of Ser. No. 6,121, Jan. 19, 1993, abandoned.
[51] Int. Cl.$^6$ .......................... A61K 38/39; A61K 38/08; A61K 38/10; C07K 17/02
[52] U.S. Cl. .................. 514/12; 514/13; 514/14; 514/15; 514/16; 514/8; 514/21; 530/325; 530/324; 530/326; 530/327; 530/328; 530/345; 530/404; 530/408; 530/405; 530/409; 530/367; 435/236
[58] Field of Search .................................... 530/326, 327, 530/328, 345, 403, 408, 409, 405, 404, 324, 325, 367; 516/12–16, 8, 21; 435/236

[56] References Cited

U.S. PATENT DOCUMENTS

| | | | |
|---|---|---|---|
| 4,703,108 | 10/1987 | Silver et al. | 530/356 |
| 5,019,646 | 5/1991 | Furcht et al. | 530/326 |
| 5,147,797 | 9/1992 | McCarthy et al. | 435/240.1 |

FOREIGN PATENT DOCUMENTS

8803810  6/1988  WIPO.

OTHER PUBLICATIONS

Fauci (1993) Science 262 : 1011–1018.
Cohen (1993) Science 262 : 980–981.
"Clinical Pharmacology" pp. 2596–2649 of *The Merck Manual of Diagnosis and Therapy* 16th edition (1992).
Danilov et al. (1989) Experimental Cell Res 182 : 186–196.
Haugen et al. (1992) J. Neurosci. 12 (6): 2034–2042.
Wilke et al. (1991) J. Invest. Dermatol. 97 (3): 573–579.
Haugen et al. (1990) J. Cell Biol. 111(6, pt. 1): 2733–45.
McCarthy et al. (1990) J. Cell Biol. 110 (3): 777–787.
McCarthy et al (1988) Biochemistry 27(4): 1380–88.
Su et al (1991) Mol. Immunol. 28 (8): 811–817.
Weeks et al. (1991) J. Cell. Biol. 114(4) : 847–53.
Taylor et al. (1992) Proc. Natl. Head Sci USA 89(20) : 9617–9621.
Kul'berg (1990) AIDS Res. Hum. Retroviruses 6(9): 1059–[0006]350115 60.
Oswald et al. (1991) FEBS Lett. 292 (1–2): 298–300.
Furcht, L T, 1983, Structure and Function of the adhesive Glycoprotein Fibronectin Mod. Cell Biol. 53–117.
Finberg, R W et al., 1991, Selective elimination of HIV–1 infected cells using an IL–2 receptor specific cytotoxin. Science 252 : 1703–1705.
Fischl, M A et al., 1987, The efficacy of AZT in the treatment of patients with AIDS and AIDS–related compex, New England J. Med. 317 : 185–191.
Hildreth, J. E. K. et al., 1989, Involvement of a leukocyte adhesion receptor (LFA–1) in HIV–induced syncytium formation. Science 244 : 1075–1078.

(List continued on next page.)

*Primary Examiner*—Kay K. A. Kim
*Attorney, Agent, or Firm*—Banner & Allegretti, Ltd.

[57] ABSTRACT

The invention includes methods for inhibiting retroviral infections such as HIV. The methods of this invention involve the use of certain fragments of fibronectin and such fragments conjugated to carrier molecules such as ovalbumin to inhibit retroviral infections. The invention also includes novel proteins which comprise fibronectin fragments covalently linked to carrier proteins.

3 Claims, 4 Drawing Sheets

OTHER PUBLICATIONS

Kalter, D. C. et al., 1991, Inhibition of human Immunodeficiency virus infection in monocytes by monoclonal antibodies against leukocyte adhesion molecules. Immunol. Lett. 30 : 219–227.

Pantaleo, G. et al., 1991, HIV infection in CD4+ T–Lymphocytes genetically deficient in LFA–1; HIV–1 is required for HIV–mediated cell fusion but not for viral transmission. J. Exp. Med. 173 : 511–514.

Pluda, J M et al., 1990, Subcutaneous recombinant granulocyte–macrophage colony–stimulating factor uses as a single agent and in an alternating regimen with azidothymidine in leukopenic patients with severe human immunodeficiency virus infection, Blood 76 : 463–472.

Rosenberg, Z F et al., 1991, Immunopathogenesis of HIV infection. FASEB J. 5 : 2382–2390.

Szebeni, J. et al., 1990, Dipyridamole potentates the activity of zidovudine and other dideoxynucleosides against HIV–1 in cultured cells. *Annals N.Y. Acad. Sci.* 626 : 613–616.

Szebeni, J. et al., 1990, Inhibition of HIV–1 in monocyte/ macrophage cultures by 2', 3'–dideoxycytidine–5'–triphosphate, free and in liposomes. *AIDS Research and Human Retroviruses* 6 : 691–702.

Wahl, S M et al., 1991, Macrophage– and Astrocyte–derived Transforming growth factor beta as a mediator of central nervous system dysfunction in acquired immune deficiency syndrom. *J. Exp. Med.* 173 : 981–991.

Weinstein; J N et al., 1991, Synergistic drug combinations in AIDS therapy. *Annals. N.Y. Acad. Sci.* 616 : 367–384.

Albeda, S M et al., 1990, Integrins and other cell adhesion molecules. *FASEB J.* 4 : 2868–2880.

Ruoslahti, E. 1991, Integrins. *J. Clin. Invest.* 87 : 1–5.

Springer; T. 1990, Adhesion receptors of the immune system. *Nature* 346: 425–434.

Verfaile, C M et al., 1991, Differentiation of primitive human multipotent hematopoietic progenitors into single––lineage clonogenic progenitors is accompanied by alterations in their interaction with fibronectin. *J. Exp. Med.* 174 : 693–703.

Wahl, L M et al., 1984, Isolation of human mononuclear cell subsets by counterflow centrifugal elution. *Cell. Immunol.* 85 : 373–383.

SYNTHETIC FIBRONECTIN FRAGMENTS AS INHIBITORS OF RETROVIRAL INFECTION

This invention was made with government support under CA-43924 and CA-21463 awarded by the National Institutes of Health. The government has certain fights in the invention.

This application is a continuation of application Ser. No. 08/006,121, filed Jan. 19, 1993, now abandoned.

BACKGROUND OF THE INVENTION

1. Field of the Invention

This invention is in the field of chemical agents and methods of inhibiting infection of cells by retrovirus.

2. Description of the Prior Art

Figure 1:
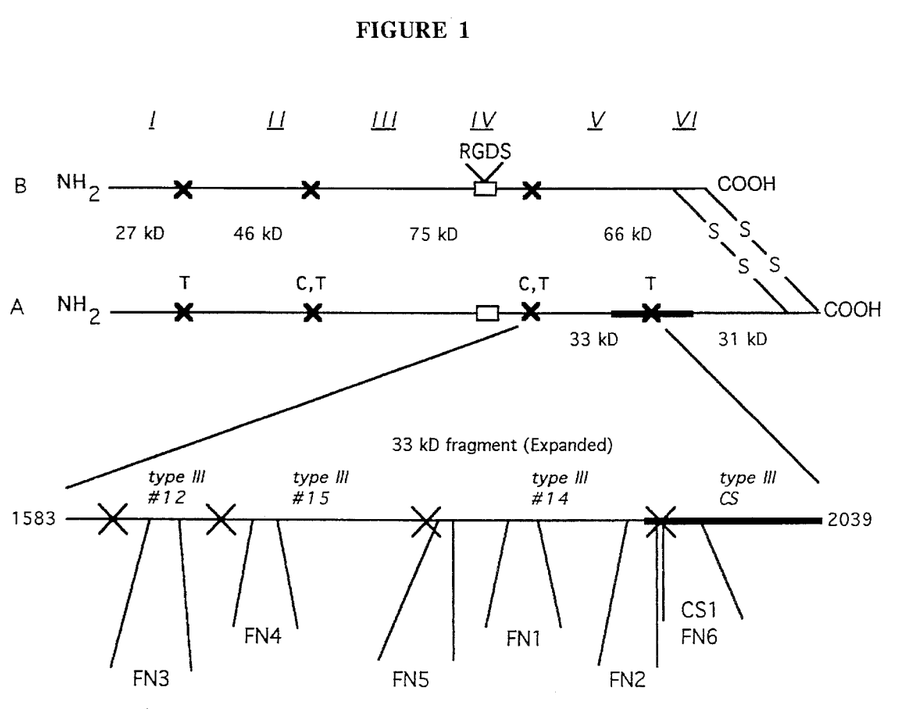
FIG. 1 shows the location of synthetic peptides within intact fibronectin.

Integrins represent a family of cell surface $\alpha\beta$ heterodimeric proteins that mediate cell adhesion to other cells and to extracellular matrix constituents including fibronectin (FN). Integrins composed of $\beta 1$ and $\beta 3$ subunits complexed to $\alpha 3$, $\alpha_v$, and $\alpha_5$ subunits interact with the arginyl-glycyl-aspartic acid (RGD) sequence of FN7 whereas $\alpha 4\beta 1$ is specific for RGD-independent sequences in the carboxyl terminal cell and heparin-binding domain of fibronectin that mediates cell attachment. However, recent evidence suggests that cellular recognition and adhesion to fibronectin domains is more complex, involving not only integrins, but also cell surface proteoglycans (PG). PG are complex macromolecules consisting of a core protein to which highly anionic glycosaminoglycan (GAG) chains are covalently attached by an O-linkage to serine or threonine residues. The anionic properties of GAG on many cell surface PG are important for binding to their respective ligands. Clearly, cell interactions with FN may involve several distinct sites, and this has been shown by the use of synthetic FN peptides. Cell binding to an A-chain-derived 33 kD carboxyl terminal heparin binding fragment of human plasma fibronectin or 66KD B chain may involve both cell surface $\alpha 4\beta 1$ integrin and PG since this FN fragment contains cationic peptides, which bind cell surface chondrortin and heparin proteoglycans (CSPG and HSPG respectively) and/or alpha and beta integrans directly. FIG. 1 shows a schematic diagram depicting the location of the 33 kD carboxyl terminal heparin binding fragment within fibronectin and the synthetic peptides described in this application. In contrast to peptides FN 1-5 and FN7, which are present within type III homologies common to all isoforms of fibronectin, peptide FN6 is restricted to isoforms of fibronectin which contain the type IIIcs region (A-chains of human plasma fibronectin and human cellular or "tissue" fibronectin). The amino terminal end and the carboxyl terminal limit of the 33 kD fragment is based on known sequence dam. Selected biological domains, indicated in FIG. 1 by roman numerals at the top of the figure, are based on the nomenclature of Furcht, 1981. I=weak heparin binding, II=collagen binding (noncovalent), III=free sulfhydryl, IV=RGD-mediated cell adhesion, V=carboxyl terminal strong heparin binding and cell adhesion, VI=free sulfhydryl. Approximate locations of tryptic (T) and cathepsin D (C) sites on intact fibronectin are shown. The $\alpha 4\beta 1$ integrin also binds to VCAM, which is an Ig superfamily receptor expressed on certain cells, including activated endothelial cells. Sequences of fibronectin peptides may interfere with alpha 4 beta VCAM dependent interactions or other integrin, selectin or CAM dependent interations.

Human immunodeficiency virus type 1 (HIV-1), a retrovirus, is the etiologic cause of AIDS. The HIV-1 envelope glycoprotein, gp120, binds to the CD4 receptor on T lymphocytes and on mononuclear phagocytes leading to infection of these target populations. Although infection of T lymphocytes requires cellular proliferation and DNA synthesis, productive infection of monocytes can occur independently of cellular DNA synthesis. Moreover, infection of activated CD4 + lymphocytes causes cell death, whereas infected monocytes are relatively resistant to destruction by the virus, serving as long-lived reservoirs of HIV.. These cells not only provide a source of replicating virus, but their dysfunction following infection may contribute to increased susceptibility to opportunistic infections that are the hallmark of AIDS. Because monocyte-macrophages serve as reservoirs for HIV-1, selective targeting of this population, in addition to T lymphocytes, needs to be considered.

Zidovudine (AZT), an analogue of thymidine, dideoxyinosine (ddi), and dideoxycytosinene, dideoxycytosine (ddc) are the primary anti-viral drugs currently in use for the treatment of HIV infection. These agents inhibit viral replication, but are unable to eliminate the virus. In addition, bone marrow toxicity, loss of efficacy with time and emergence of resistant HIV strains with available therapies have necessitated continued exploration for alternative drugs for the treatment of HIV infection. We have recently identified a novel mechanism for inhibiting HIV infection utilizing fibronectin and/or its fragments which provide the basis for therapeutic intervention. There is an extensive body of literature related to AIDS research.

Furcht, L. T. 1981, Structure and Function of the adhesive Glycoprotein Fibronectin Mod. Cell Biol. 53–117.

Finberg, R. W., Wahl, S. M., Allen, J. B., Soreart, G., Strom, T. B., Murphy, J. R., and Nichols, J. C. 1991. Selective elimination of HIV-1 infected cells using an IL-2 receptor specific cytotoxin Science. 252:1703–1705.

Fischl, M. A., et al.: 1987. New Engl. J.Med. 317:185–191.

Hildreth, J. E. K., Orentas, R. J.: 1989. Involvement of a leukocyte adhesion receptor (LFA-1) in HIV-induced syncytium formation. Science 244:1075–1078.

Kalter, D. C., Gendelman, H. E., Meltzer, M. S.: 1991. Inhibition of human immunodeficiency virus infection in monocytes by monoclonal antibodies against leukocyte adhesion molecules. Immunol Lett. 30:219–227.

Pantaleo, G., Butini, L., Graziosi, C., Poli, G., Schmittman, S. M.: 1991. Human immunodeficiency virus (HIV) infection in CD4+ T-lymphocytes genetically deficient in LFA-1; HIV-1 is required for HIV-mediated cell fusion but not for viral transmission. J.Exp. Med. 173:511–514.

Pluda, J. M., Yarchoan, R., McAtee, N., Smith, P. D., Thomas, R., Oette, D., Maha, M., Wahl, S. M., Myers, C., and Broder, S., 1990. A feasibility study using an alternating regiment of azidothymidine (AZT) and recombinant granulocyte-macrophage colony stimulating factor (GM-CSF) in patients with severe human immunodeficiency virus (HIV) infection and leukopenia. Blood. 76:463–472.

Rosenberg, Z. F. and Fauci, A. S. 1991. Immunopathogenesis of HIV infection. FASEB J. 5:2382.

Szebeni, J., Wahl, S. M., Schinazi, R. F., Popovic, M., Gartner, S., Wahl, L. M., Weislow, O. S., Betageri, G., Fine, R. L., Dahlberg, J. E., Hunter, B. and Weinstein, J. N.: 1990. Dipyridamole potentiates the activity of zidovudine and other dideoxynucleosides against HIV-1 in cultured cells. Annals of New York Academy of Sciences. 626:613–616.

Szebeni, J., Wahl, S. M., Wahl L. M., Gartner, S., Popovic, M., Parker, R., Black, C. D., and Weinstein, J. N.: 1990. Inhibition of HIV-1 in monocyte/macrophage cultures by 2',3'-dideoxycytidine-5'-triphosphate, free and in liposomes. AIDS Research and Human Retroviruses. 6:691–702.

Valentin, A., Lundin, K., Patarroyo, M., Asjo, B.: 1990b. The leukocyte adhesion glycoprotein, CD18, participates in HIV-1 induced syncytia formation in monocytoid cells and T-cells. 1. Exp. Med. 173:511–514.

Wahl, S. M., Allen, J. B., McCartney-Francis, N. Morganti-Kossmann, M. C., Kossmann, T., Ellingsworth, L., Mergenhagen, S. E., and Orenstein, J. M.: 1991. Transforming growth factor beta. A potential macrophage and astrocyte-derived mediator of CNS dysfunction in AIDS. Journal of Experimental Medicine. 173:89 1–899.

Wahl, S. M., Allen, J. B., Gartner, S., Orenstein, J. M., Chenoweth, D. E., Popovic, M., Arthur, L. O., Farrar, W. L., and Wahl, L. M.: 1989. Human immunodeficiency virus and its envelope glycoprotein down-regulate chemotactic ligand receptors and chemotactic function of peripheral blood monocytes. Journal of Immunology. 142:3553–3559.

Weinstein, J. N., Bunow, B., Welslow, O. S., Schinazi, R. F., Wahl, S. M., Wahl, L. M., and Szebeni, J.: 1991. Synergistic drug combinations in AIDS therapy: Dipyridamole-azidothymidine in particular and principles of analysis in general. Annals of New York Academy of Sciences. 616:367–384.

Albelda, S. M. and Buck, C. A. 1990. Integrins and other cell adhesion molecules. FASEB J. 4, 2668–2680.

Haugen, P. K., McCarthy, J. B., Skubitz, A. P. N., Furcht, L. T. and Letourneau, P. C. 1990. Recognition of the A-chain carboxyl-terminal heparin-binding region of fibronectin involves multiple sites: two contiguous sequences act independently to promote neural cell adhesion. *J. Cell Biol.* 111:2733–2745.

McCarthy, J. B., Mickelson, D. L., Chelberg, M. K. and Furcht, L. T. 1988. Localization and chemical synthesis of fibronectin peptides with melanoma adhesion and heparin-binding activities. *Biochemistry* 27:1380–1388.

Ruoslahti, E. 1991. Integrins. *J. Clin. Invest.* 87:1–5.

Springer, T. 1990. Adhesion receptors of the immune system. *Nature* 346:425–434.

Verfaile, C. M., McCarthy, J. B. and MeGlave, P. B. 1991. Differentiation of primitive human multipotent hematopoietic progenitors into single-lineage clonogenic progenitors is accompanied by alterations in their interaction with fibronectin. *J. Exp. Med.* 174:693–703.

Wahl, L. M., Katona, I. M., Wilder, R. L., Winter, C. C., Haraoui, B., Scher, I. and Wahl, S. M. 1984. Isolation of human mononuclear cell subsets by counterflow centrifugal elution. Characterization of β-lymphocytes, T-lymphocytes and monocyte-enriched fractions by flow cytometric analysis. *Cell. Immunol.* 85:373.

Wilke, M. S., Skubitz, A. P. N., Furcht, L. T. and McCarthy, J. B. 1991. Human keratinocytes adhere to two distinct heparin-binding synthetic peptides derived from fibronectin. *J. Invest. Derm.* 97:573–579.

Su et at., *Mol. Immunology*, August 1991, 28(8):811–817 describe the binding of fibronectin to gp 120.

SUMMARY OF THE INVENTION

This invention describes the use of fibronectin fragments and conjugates with carder molecules thereof for preventing or treating retroviral infections and associated diseases including AIDS. Selected peptides derived from fibronectin are effective inhibitors of HIV infection, replication and/or transmission. Addition of fibronectin peptides to cultures of human peripheral blood mononuclear leukocytes during exposure to HIV results in inhibition of infection as measured by reverse transcriptase activity in the cultures when compared to untreated infected cultures. This activity demonstrates the ability of the peptides to block viral adherence to and infection of mononuclear leukocytes.

More specifically, the invention encompasses carrier molecules covalently linked to an amino acid sequence selected from the group consisting of FN 1, 2, 3, 4, 5, 6 and 7 as herein after defined. The invention also encompasses pharmaceutical compositions for treating retroviral infection. The invention also encompasses methods for inhibiting retrovirus infection of mammalian cells by contacting the cells with an effective inhibiting amount of FN 1, 2, 3, 4, 5, 6 or 7 or these peptides conjungated to a carrier molecule. Furthermore, this invention encompassses the use of the compounds with conventional AIDS therapy such as AZT, ddi, and ddc. Those skilled in this art will recognize that peptides homologous to the above fragments, their derivatives and their conjugates with carrier molecules will have equivalent activity.

DETAILED DESCRIPTION OF THE INVENTION

The present invention provides methods for preventing retrovirus infection, particularly HIV infection of mammalian cells, and associated diseases. Two of these synthetic peptides (FN-1 and FN-2) which are also in the B chain of fibronectin bind heparin and promote cell adhesion, implicating cell surface PG or other carbohydrate binding molecules in mediating cellular recognition of these two peptides. Additionally, a third synthetic peptide, FN-6, is located in close proximity to FN-1 and FN-2 and it promotes cell adhesion by an $\alpha 4\beta 1$ integrin-dependent mechanism. Additional peptides from within the 33 kD fragment of the A-chain and are also seen in the B-chain (FN-3, FN-4, FN-5) also influence cell adhesion properties. In addition to influencing cell-virus interactions and cell to cell interactions, functional adhesion molecules and cell-matrix interactions have been shown to be vital to localization of immune and infected cells to target tissues. This increased adhesion to the basement membrane proteins, laminin and Type IV collagen, as well as fibronectin, implicate these pathways in coordinating the early margination, recruitment and migration of leukocytes to tissue sites with the potential for viral spread. Consequently, methods to interfere with these pathways and their contribution to the immune deficiency syndrome have a beneficial effect on this devastating disease.

Mononuclear leukocytes ($10^7$) were co-cultured with macrophage tropic $HIV_{Ba-L}$ in adherent monolayers. The cells were then washed and re-fed in DMEM (Gibco Laboratories, Grand Island, N.Y.) with 50 µg/ml gentamicin, 2 mM glutamine, containing 10% FCS. Media (50%) were removed and fresh medium added at 3–4 day intervals. Infection was monitored measuring by reverse transcriptase (RT) at 3- to 4-day intervals.

Peptides FN-1, 2, 3, 4, 5, 6, 7 were coupled to ovalbumin (OA) as a biological carder molecule using 1-Ethyl-3-[3-Dimethylominopropyl]-carbodiimide, hydrochloride, dialyzed, and diluted in phosphate-buffered saline to provide conjugated peptides FN-C/H-I, II, III, IV, V, MC-2 and CS1.

TABLE I

FEBRONECTIN PEPTIDES AND BIOLOGICAL CARRIER MOLECULE CONJUGATES THEREOF

| (Fibronectin Fragment) | | Ovalbumin Conjugate |
|---|---|---|
| FN1 | (1906–1924) SEQ ID NO. 1 YEKPGSPPREWPRPRPGV | FN-C/H-I |
| FN2 | (1946–1960) SEQ IID NO. 2 KNNQKSEPLIGRKKT | FN-C/H-II |
| FN3 | (1721–1960) SEQ ID NO. 3 YRVRVTPKEKTGPMKE | FN-C/H-III |
| FN4 | (1784–1792) SEQ ID NO. 4 SPPRRARVT | FN-C/H-IV |
| FN5 | (1892–1899) SEQ ID NO. 5 WQPPRARI | FN-C/H-V |
| FN6 | (1961–1985) SEQ ID NO. 6 | CS-1 |
| FN7 | (1485–1504) SEQ ID NO. 7 ITVYAVTGRGDSPASSKPISI | MC-2 |

U.S. Pat. Nos. 5,019,646; 5,116,368; and 4,839,464 describe peptide fragments from fibronectin which are useful in the present invention.

Human peripheral blood mononuclear cells were isolated from leukophoresis units (NIH Department of Transfusion Medicine) by Ficoll-Hypaque density gradient centrifugation followed by counterflow centrifugal elutriation. The adherent cells were co-cultured with HIV in the presence or absence of anti-CD4 (5 µg/ml) and the peptides CS-1 and MC-2 (20 µg/ml). After washing the cells, aliquots of supernatants were harvested at 3–4 day intervals and analyzed for reverse transcriptase activity. Supernatants from the infected cultures were assayed directly for RT activity by a micromethod modified from Spira and co-workers. (J. Geyer and J. S. Apstein, Fifth International Conference on AIDS, International AIDS Society, Montreal, Canada. Jun. 4 to 9, 1989, p. 636. (abstr. Th.C.P. 118). *T. J. Spira et al., J. Clin. Microbiol*, 25,97 (1987).

Figure 2:
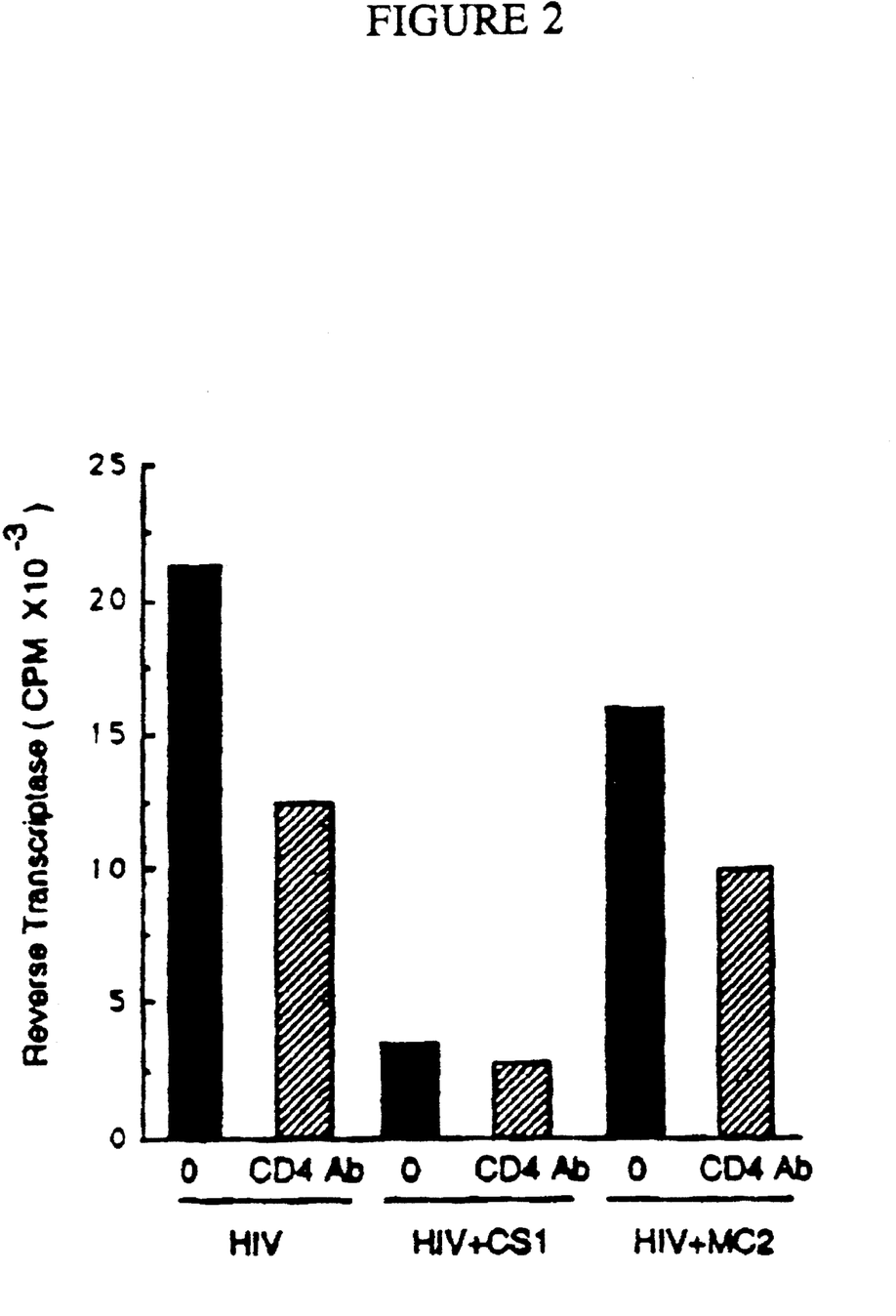
FIG. 2 shows the inhibition of HIV infection by fibronectin peptides and anti CD4.
Figure 3:
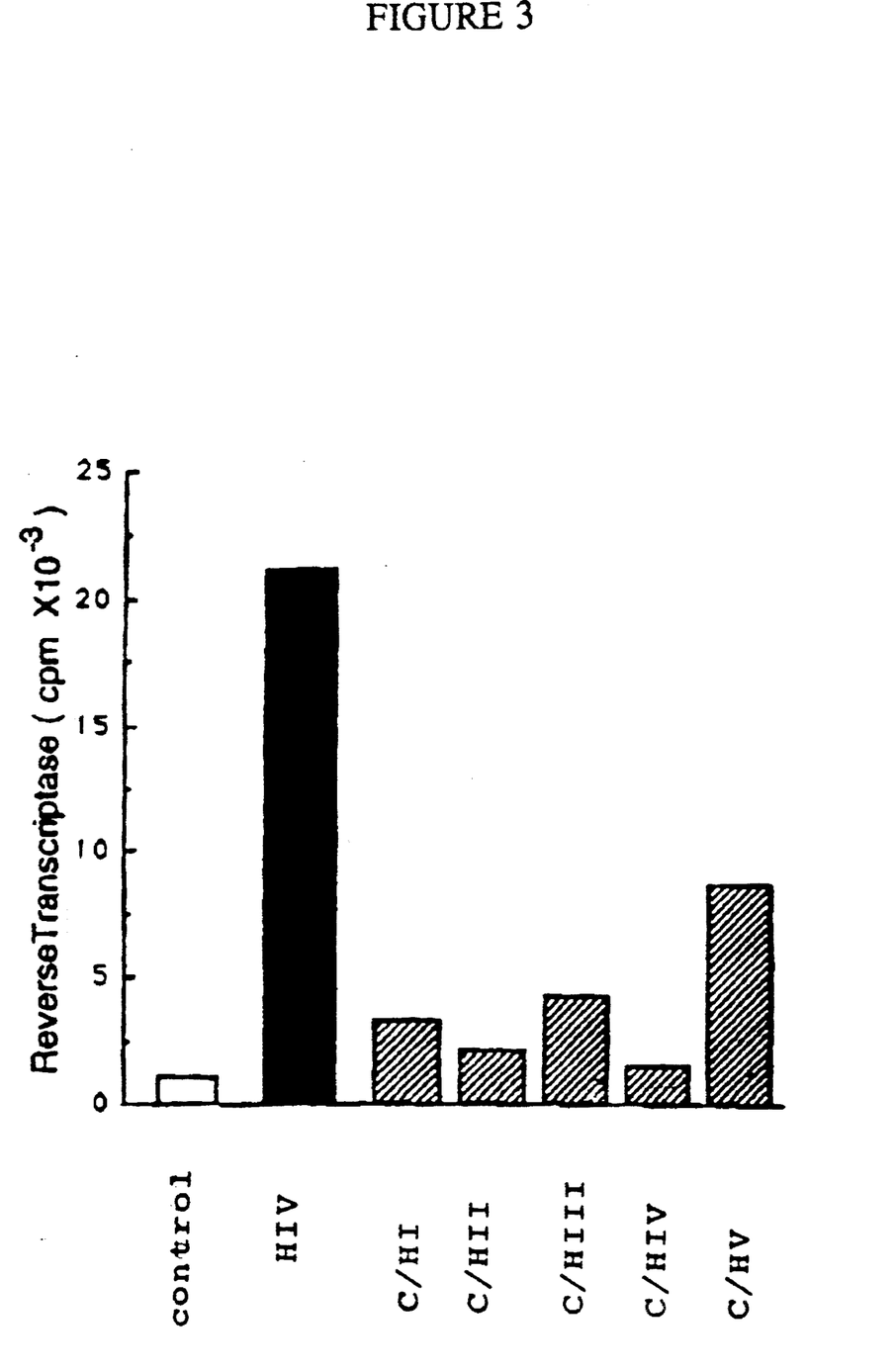
FIG. 3 shows fibronectin peptides inhibiting HIV infection.

As evident in FIG. 2, the CS-1 peptide was more effective than the RGD-containing (MC-2) peptide at inhibiting viral infection as monitored by RT activity in the supernatants of cultures infected with HIV. Inhibition was augmented in the presence of anti-CD4. Non-overlapping domains of the 33 kDA fragment of fibronectin also demonstrate suppression of viral infection. FIG. 3 compares the reverse transcriptase activity of control cells and cells treated with HIV, C/H-I, C/H-II, C/H-III, C/H-IV and C/H V. Mononuclear leukocytes isolated and cultured as in FIG. 2 were infected with HIV in the presence of the indicated peptides at 20 µg/ml. Supernatants were monitored for reverse transcriptase activity.

Figure 4:
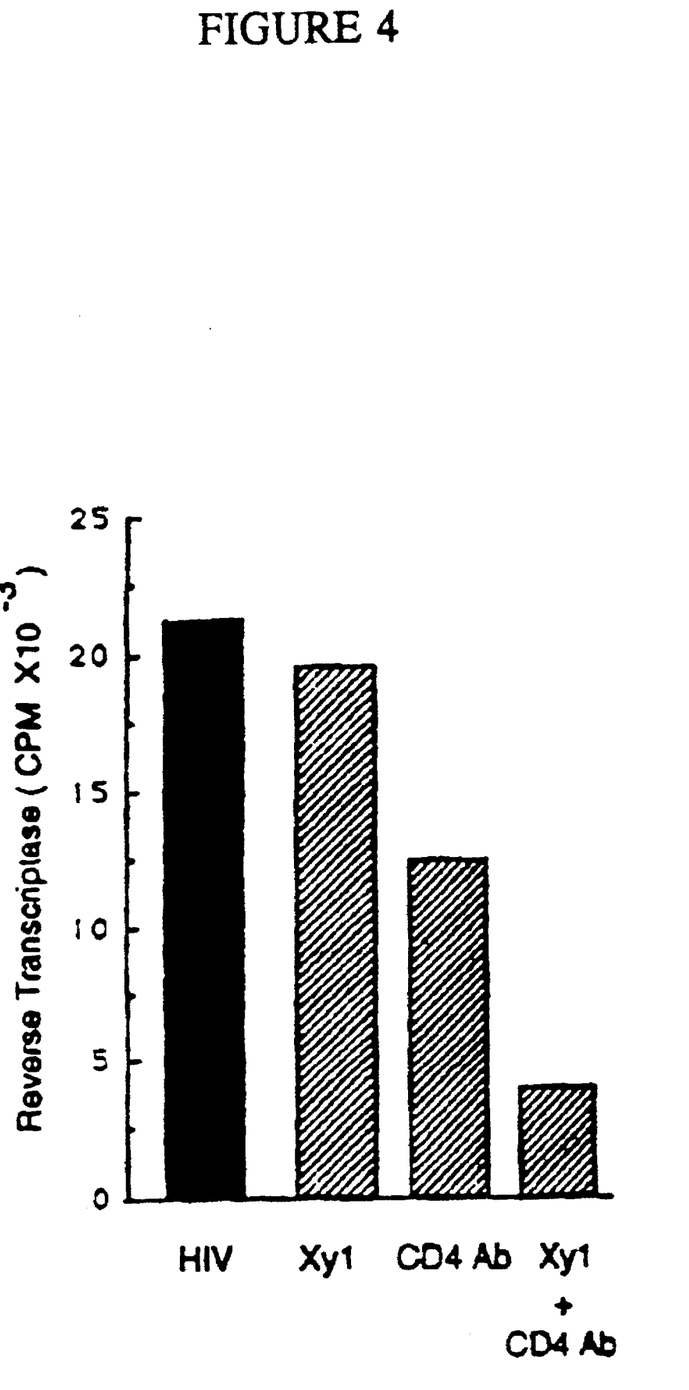
FIG. 4 shows how xyloside augments anti CD4 inhibition of HIV infection.

In addition, treatment of the mononuclear leukocytes with xyloside which interferes with proteoglycan expression and function, while not independently inhibiting HIV infection of mononuclear leukocytes, acts synergistically with anti-CD 4 to block infection, as shown in FIG. 4. In this study, mononuclear leukocytes were pre-treated with xyloside (1 ml) for 18 hr and then co-cultured with HIV in the presence or absence of anti-CD4 (5 µg/ml). Supernatants were monitored for reverse transcriptase activity. These data suggest that binding to monocytes and/or other target cells may involve co-receptor interactions and/or receptor clustering.

Based on these anti-viral activities, the peptides have important therapeutic applications. The heparin-binding properties of FN-C/H-I, II and V suggest that they bind to cell surface PG or other molecules on mononuclear leukocytes in addition to integrins, and the identification of this novel heparin-dependent adhesion interaction provides insight into leukocyte infection mechanisms.

Polypeptides synthesized can be employed in the present invention in a monovalent state (i.e., free polypeptide or single polypeptide fragment coupled to a biological carrier molecule such as collagen, albumin or other biological or synthetic carrier molecules). Preferably, as described below, conjugates of multiple polypeptide fragments bound to a biological carder molecule such as ovalbumin (OA), human serum albumin (HSA) and similar proteins. Other biologically acceptable carder molecules such as polyethylene glycol (PEG) or the like may be utilized. The number of polypeptide fragments associated with or bound to each carrier molecule can be varied, but from about 5 to about 8 polypeptide fragments per carrier molecule are obtained under these coupling conditions. Such modifications can alter the affinity and half-life of the peptide. Antiretroviral agents are generally efficacious in doses ranging from 50 mg/day to about 500 mg/day.

The sterile injectable preparation may be a sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono-or diglycerides. In addition, fatty acids such as oleic acid find use in the preparation of injectables.

It will be understood, however, that the specific dose level for any particular patient will depend upon a variety of factors including the activity of the specific compound employed, the age, body weight, general health, sex, diet, time of administration, mute of administration and rate of excretion.

EXAMPLE 1

General Procedure for Coupling Peptides to Ovalbumin

In a small polypropylene tube add X mg of lyophilized peptide and mg of ovalbumin. These proteins are dissolved in water such that the concentration of protein is 2–4 mg of protein per ml of water. In a second polypropylene tube add 10X mg (ten times the peptide mount) of EDC (1-Ethyl-3-[3-Dimethylominopropyl]-carbodinmide), hydrochloride. The EDC is dissolved in the smallest possible amount of water (to about 25 ul for 20 mg final of EDC) and this solution is added to the tube containing the peptide/ovalbumin mixture. This coupling reaction mixture is mixed in a circular rotator for a minimum of 2 hours at 4° C. The reaction mixture is transferred to dialysis tubing with a 10,000 molecular weight cut-off and dialyzed into 4 liter of Dulbecco's phosphate buffered saline, pH 7.4 (PBS). The dialysis solution is changed every 6 to 8 hours several times to remove the EDC and uncoupled peptides. The volume is adjusted to achieve about 2 mg/ml. of peptide. Aliquots of peptide-conjugate are frozen at −80° C.

EXAMPLE 2

Treatment of Cells and Measurement of HIV Replication

The fibronectin-derived peptide (20 μl at 2 μg/ml which equals 40 μg/μl final was added during the time of exposure of the mononuclear leukocytes to HIV. The cultures were re-fed at 3- to 5-day intervals by substituting half of the cell supernatant (500 μl) with fresh medium. Supernatant samples were analyzed (or HIV-1 reverse transcriptase (RT) supernatants from the infected and control adherent mononuclear leukocytes cultures were assayed directly for RT activity by a micromethod modified from Spira and co-workers. J. Geyes and J. S. Epstein, Fifth International Conference on AIDS, International AIDS Society, Montreal, Canada 4 to Jun. 9, 1989, p. 636 (abstr. Th.C.P. 118). T. J. Spira et al., J. Clin. Microbiol. 27, 97 (1987).

The above examples are intended to illustrate the present invention and not to limit it in spirit or scope.

What is claimed is:

1. A method for inhibiting HIV-1 virus infection of mammalian cells comprising contacting the cells with an effective inhibiting amount of a fibronectin fragment or carrier molecule conjugates thereof, where the fibronectin fragment amino acid sequence is selected from the group consisting of:

YEKPGSPPRE WPRPRPGV (FN1; SEQ ID NO:1), KNNQKSEPLI GRKKT (FN2; SEQ ID NO:2), YRVRVTPKEK TGPMKE (FN3; SEQ ID NO:3), SPPRRARVT (FN4; SEQ ID NO:4), and WQPPRARI (FN5; SEQ ID NO:5). D[P]ELPQLVTLP HPNLHG-PEIL DVPST (FN6; SEQ ID NO:6), and ITVYAVT-GRG DSPASSKPISI (FN7; SEQ ID NO:7).

2. The method of claim 1 wherein zidovudine (AZT), dideoxyinosine, dideoxycytosinene, or dideoxycytosine is used in combination with the fibronectin fragment or carrier molecule conjugate thereof.

3. A method according to claim 1 wherein the carrier molecule is ovalbumin.

* * * * *

UNITED STATES PATENT AND TRADEMARK OFFICE
CERTIFICATE OF CORRECTION

PATENT NO. : 5,545,620
DATED : August 13, 1996
INVENTOR(S) : Wahl, et. al.

It is certified that error appears in the above-indentified patent and that said Letters Patent is hereby corrected as shown below:

At column 12, line 24

The "D[P]ELPQLVTLP" should read - -DELPQLVTLP- -

Signed and Sealed this

Twenty-second Day of October, 1996

Attest:

BRUCE LEHMAN

*Attesting Officer*   *Commissioner of Patents and Trademarks*

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 19 amino acids
        ( B ) TYPE: amino acid
        ( C ) STRANDEDNESS: single
        ( D ) TOPOLOGY: linear     ( i i ) MOLECULE TYPE: peptide     ( i x ) FEATURE:
        ( A ) NAME/KEY: Peptide
        ( B ) LOCATION: 1..19
        ( D ) OTHER INFORMATION: /note="FN1 (1906-1924) fibronectin fragment : FN-C/H-I"

( x i ) SEQUENCE DESCRIPTION: SEQ ID NO:1:

Tyr Glu Lys Pro Gly Ser Pro Pro Arg Glu Val Val Pro Arg Pro Arg
1               5                   10                  15

Pro Gly Val ( 2 ) INFORMATION FOR SEQ ID NO:2:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear     ( i i ) MOLECULE TYPE: peptide     ( i x ) FEATURE:
        ( A ) NAME/KEY: Peptide
        ( B ) LOCATION: 1..15
        ( D ) OTHER INFORMATION: /note="FN2 (1946-1960) fibronectin fragment : FN-C/H-II"

( x i ) SEQUENCE DESCRIPTION: SEQ ID NO:2:

Lys Asn Asn Gln Lys Ser Glu Pro Leu Ile Gly Arg Lys Lys Thr
1               5                   10                  15

( 2 ) INFORMATION FOR SEQ ID NO:3:

( i ) SEQUENCE CHARACTERISTICS:
        ( A ) LENGTH: 16 amino acids
        ( B ) TYPE: amino acid
        ( C ) STRANDEDNESS: single
        ( D ) TOPOLOGY: linear     ( i i ) MOLECULE TYPE: peptide ( i x ) FEATURE:
    ( A ) NAME/KEY: Peptide
    ( B ) LOCATION: 1..16
    ( D ) OTHER INFORMATION: /note="FN3 (1721-1960)
        fibronectin fragment : FN-C/H-III"

( x i ) SEQUENCE DESCRIPTION: SEQ ID NO:3:

Tyr Arg Val Arg Val Thr Pro Lys Glu Lys Thr Gly Pro Met Lys Glu
1               5                   10                  15

( 2 ) INFORMATION FOR SEQ ID NO:4:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear     ( i i ) MOLECULE TYPE: peptide     ( i x ) FEATURE:
        ( A ) NAME/KEY: Peptide
        ( B ) LOCATION: 1..9
        ( D ) OTHER INFORMATION: /note="FN4 (1784-1792)
            fibronectin fragment : FN-C/H-IV"

( x i ) SEQUENCE DESCRIPTION: SEQ ID NO:4:

Ser Pro Pro Arg Arg Ala Arg Val Thr
1               5

( 2 ) INFORMATION FOR SEQ ID NO:5:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear     ( i i ) MOLECULE TYPE: peptide     ( i x ) FEATURE:
        ( A ) NAME/KEY: Peptide
        ( B ) LOCATION: 1..8
        ( D ) OTHER INFORMATION: /note="FN5 (1892-1899)
            fibronectin fragment : FN-C/H-V"

( x i ) SEQUENCE DESCRIPTION: SEQ ID NO:5:

Trp Gln Pro Pro Arg Ala Arg Ile
1               5

( 2 ) INFORMATION FOR SEQ ID NO:6:

( i ) SEQUENCE CHARACTERISTICS:
        ( A ) LENGTH: 25 amino acids
        ( B ) TYPE: amino acid
        ( C ) STRANDEDNESS: single
        ( D ) TOPOLOGY: linear     ( i i ) MOLECULE TYPE: peptide     ( i x ) FEATURE:
        ( A ) NAME/KEY: Peptide
        ( B ) LOCATION: 1..25
        ( D ) OTHER INFORMATION: /note="FN6 (1961-1985)
            fibronectin fragment : CS-1"

( x i ) SEQUENCE DESCRIPTION: SEQ ID NO:6:

Asp Glu Leu Pro Gln Leu Val Thr Leu Pro His Pro Asn Leu His Gly
1               5                   10                  15

Pro Glu Ile Leu Asp Val Pro Ser Thr
                20                  25

( 2 ) INFORMATION FOR SEQ ID NO:7:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear     ( i i ) MOLECULE TYPE: peptide     ( i x ) FEATURE:
        ( A ) NAME/KEY: Peptide
        ( B ) LOCATION: 1..19
        ( D ) OTHER INFORMATION: /note="FN7 (1485-1504)
            fibronectin fragment : MC-2"

( x i ) SEQUENCE DESCRIPTION: SEQ ID NO:7:

```
Ile Thr Val Tyr Ala Val Thr Gly Arg Gly Asp Ser Pro Ala Ser Ser
 1               5                  10                  15

Lys Pro Ile Ser Ile
             20
```